(12) United States Patent
Bartorelli et al.

(10) Patent No.: US 9,248,151 B2
(45) Date of Patent: Feb. 2, 2016

(54) MULTIPURPOSE GEL FOR VAGINAL DRYNESS WITH DIRECT AND DELAYED EFFECT

(75) Inventors: Alberto Bartorelli, Crans sur Sierre (CH); Maria Rosa Gobbi, Fino Mornasco (IT)

(73) Assignee: ZAMBON S.P.A., Bresso (IT)

( * ) Notice: Subject to any disclaimer, the term of this patent is extended or adjusted under 35 U.S.C. 154(b) by 89 days.

(21) Appl. No.: 13/992,037

(22) PCT Filed: Dec. 2, 2011

(86) PCT No.: PCT/EP2011/071612
§ 371 (c)(1),
(2), (4) Date: Jun. 24, 2013

(87) PCT Pub. No.: WO2012/076409
PCT Pub. Date: Jun. 14, 2012

(65) Prior Publication Data
US 2014/0322329 A1   Oct. 30, 2014

(30) Foreign Application Priority Data
Dec. 9, 2010 (IT) ............................. MI2010A2260

(51) Int. Cl.
| | | |
|---|---|---|
| *A61K 35/20* | (2006.01) | |
| *A61K 31/16* | (2006.01) | |
| *A61K 31/355* | (2006.01) | |
| *A61K 36/31* | (2006.01) | |
| *A61K 36/88* | (2006.01) | |
| *A61K 31/14* | (2006.01) | |
| *A61K 38/17* | (2006.01) | |
| *A61K 9/00* | (2006.01) | |
| *A61K 9/06* | (2006.01) | |
| *A61K 31/164* | (2006.01) | |
| *A61K 31/205* | (2006.01) | |
| *A61K 36/886* | (2006.01) | |
| *A61K 45/06* | (2006.01) | |
| *A61K 47/46* | (2006.01) | |

(52) U.S. Cl.
CPC ............... *A61K 35/20* (2013.01); *A61K 9/0031* (2013.01); *A61K 9/06* (2013.01); *A61K 31/14* (2013.01); *A61K 31/16* (2013.01); *A61K 31/164* (2013.01); *A61K 31/205* (2013.01); *A61K 31/355* (2013.01); *A61K 36/31* (2013.01); *A61K 36/88* (2013.01); *A61K 36/886* (2013.01); *A61K 38/17* (2013.01); *A61K 38/1767* (2013.01); *A61K 45/06* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 2003/0215506 A1 | 11/2003 | Kuhrts | |
| 2006/0233884 A1 | 10/2006 | Balazs | |
| 2008/0113031 A1* | 5/2008 | Moodley et al. | ............... 424/490 |
| 2009/0317378 A1 | 12/2009 | Perraudin | |
| 2011/0178488 A1 | 7/2011 | Balazs | |
| 2011/0200610 A1 | 8/2011 | Ilan et al. | |
| 2011/0236445 A1 | 9/2011 | Cilurzo et al. | |

FOREIGN PATENT DOCUMENTS

WO    2007039124    4/2007

OTHER PUBLICATIONS

J. Bojkovski, et al., Colostrum Composition Before and After Calving . . . , The Veterinary Record, 2005.
B. Albertini, et al., Polymer-Lipid Based Mucoadhesive Microspheres . . . , European Journal of Pharm. Sci., vol. 36, pp. 591-601, 2009.
S. Patil, et al., Mucoadhesive Microspheres: A Promising . . . , Current Drug Delivery, vol. 5, pp. 312-318, 2008.
K. Pattabhi, et al., Mucoadhesive Microspheres for Controlled . . . , Biol. Pharm. Bull. vol. 11, pp. 1717-1724, 2004.

* cited by examiner

*Primary Examiner* — Brian J Gangle
*Assistant Examiner* — Andrea McCollum
(74) *Attorney, Agent, or Firm* — Silvia Salvadori, P.C.; Silvia Salvadori (57) ABSTRACT

The present invention relates to topical vaginal compositions in gel form containing immune mediators, growth factors, chemotactic factors and antibacterial/antiviral factors extracted from bovine colostrum, and optionally other ingredients with complementary activity.

5 Claims, 7 Drawing Sheets

FIGURE 1

INCREASE IN MICROBIAL CONTAMINATION FROM START
OF COLLECTION DURING FREEZING TIME

FIGURE 2

RELATIONSHIP BETWEEN MICROBIAL CONTAMINATION AND CONCENTRATION OF PRESERVATIVES

|  | TAMC (CFU/g) | TYMC (CFU/g) |
|---|---|---|
| Colostrum without preservatives | 1650000 | 20975 |
| Colostrum with potassium sorbate and sodium benzoate at the concentration of 0.2% | 1316000 | 3720 |
| Colostrum with potassium sorbate and sodium benzoate at the concentration of 2% | 3600 | 10 |
| Colostrum with potassium sorbate and sodium benzoate at the concentration of 4% | 120 | < 10 |
| Colostrum with potassium sorbate and sodium benzoate at the concentration of 25% | 20 | < 10 |

TAMC: total aerobic microbial count

TYMC: total yeast and mould count

PRE-treatment 100 microns

FIGURE 7

MULTIPURPOSE GEL FOR VAGINAL DRYNESS WITH DIRECT AND DELAYED EFFECT

This application is a U.S. national stage of PCT/EP2011/071612 filed on
Dec. 2, 2011, which claims priority to and the benefit of Italian Application No. MI2010A002260, filed on Dec. 9, 2010, the contents of which are incorporated herein by reference.

The present invention relates to topical vaginal compositions in gel form containing immune mediators, growth factors, chemotactic factors and antibacterial/antiviral factors extracted from bovine colostrum, and optionally other ingredients with complementary activity.

PRIOR ART

Under physiological conditions, the vaginal ecosystem is a dynamic balance of microbial flora modulated by the hormone balance, the pH and the immune response, which are closely interdependent factors. The cells of the vaginal wall play an important role in maintaining said balance, especially the surface and intermediate layers of the epithelium, whose proliferation and maturity is hormone-related.

The vaginal mucosa is normally moistened by fluid, visible on inspection as a clear secretion consisting of plasma transudate, cervical mucus and vestibular gland secretions. Said fluid also contains antimicrobial substances which give it the function of a protective interface. 5% of the vaginal secretion consists of vaginal transudate, and 95% of cervical mucus and the secretions that flow into it. The mucus prevents microbial colonisation by means of mechanical action, through its properties of viscosity and elution, and because it contains antibodies (IgG and IgA), cytokines and antibacterial factors.

"Vaginal dryness" is a frequent condition at menopausal age; it is less common but equally unpleasant when it affects patients of childbearing age.

While menopausal hypoestrogenism and urinary habits are the prevalent factors in elderly women, in women of childbearing age the causes can also be represented by the use of low-dose combined oestrogen-progestogen contraceptives, tampons, stress, etc.

The symptoms consist of pain, stinging and itching, particularly during sexual intercourse, and tend to persist. Bartolini's and Skene's glands should produce mucus; this is essential as a "lubricating fluid", which is useful for normal performance of sexual intercourse. However, when the disorder is present, this production does not take place, thus causing discomfort for the patient. Poor vaginal and vulvar lubrication often causes a series of disorders in women, such as stinging, itching and dyspareunia. There is also greater sensitivity to even modest irritant stimuli, and more frequent episodes of vaginosis and vaginitis. The disorder is quite frequently associated with urination disorders, in the form of urinary stinging. A frequent colposcopy finding is irregular iodine uptake on the Schiller Test.

Numerous hormone-based medicaments have been proposed for the treatment of these disorders. Unfortunately, there is a suspicion of increased incidence of breast tumours, especially comedocarcinoma, for all these products. Many products based on phytoestrogens have been proposed, but scientific evidence of a breast cancer risk also exists in these cases: soya isoflavones induce 97% proliferation of the murine MCF-7 tumour line compared with the controls.

There is consequently a need for a product based on natural substances which:
- do not alter the vaginal ecosystem but help to restore and maintain the balance, and boost its defences;
- are presented in a gel formulation similar to the physiological vaginal secretion and give immediate relief, at the same time promoting the reconstruction and maintaining the integrity of the mucosa;
- release part of the active ingredients quickly and part on a slow-release basis so as to produce a long-lasting therapeutic effect covering the period between successive administrations.

DESCRIPTION OF THE INVENTION

It has now been discovered that these aims are achieved by a formulation containing, as active ingredient, a colostrum fraction enriched with immunoglobulins, growth factors, chemotactic factors and antibacterial/antiviral factors, partly in free, prompt-release form and partly in controlled-release form, preferably encapsulated in mucoadhesive microbeads.

Mucoadhesive microspheres are commercially available under the name SPHERULITE®, or can be prepared according to WO 2010060886.

The compositions according to the invention preferably contain other ingredients, especially panthenol, betaine, sericin, vitamin E, *Lepidium mehenii* (Maca) extract, and *Aloe vera*.

The compositions according to the invention are advantageously used to treat premenopausal, menopausal and hysterectomised women, teenage girls, postpartum or breastfeeding women, women suffering from stress-related dryness and women who make excessive use of imbalanced local treatments.

The colostrum fraction usable in the gel according to the invention is obtainable from bovine colostrum, in particular from Holstein (Friesian) and Guernsey cows. It has been demonstrated that these cows produce the colostrum with the highest concentration of growth factors, immune modulators, chemotactic factors and antibacterial/antiviral factors. The cows are preferably calving for the second or third time. The colostrum is preferably collected between the 5th and 6th hour after calving (colostrum 5H), because the highest concentration of active substances is found during that period. The colostrum collected in the first hour contains a lower concentration of active substances, while from the sixth hour onwards the active factors decline rapidly (only 15% are present 24 hours after calving).

The colostrum 5H collected is tested for tuberculosis, cytoxocity on cell cultures, mycoplasma, prions and human and bovine viruses.

Figure 1:
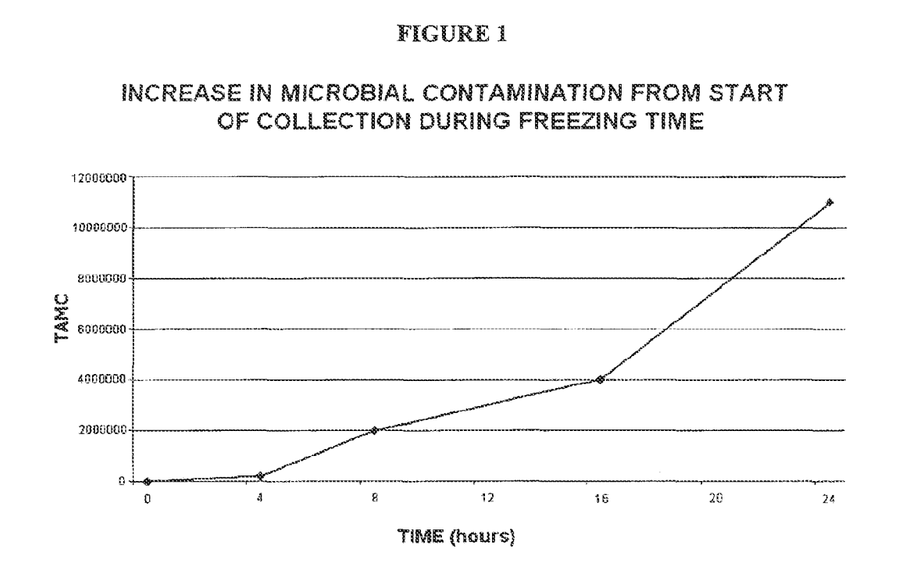
FIG. 1 shows the increase in microbial contamination from start of collection of the colostrum during freezing time.

The colostrum in the udder cistern is practically sterile, but once milked, despite all precautions, due to the high concentration of growth factors, its bacteria count rises very rapidly during freezing and thawing, which are rather slow processes in view of the high density of colostrum in the first few hours (FIG. 1).

The concentration of preservatives allowed for dietary use and those allowed for parenteral and/or intravenous use is not sufficient to stop the bacteria count. The use of γ rays only produces sterile colostrum if radiation exceeding 10 Kgy is used, but this destroys a large part of the active factors, and in any event this method does not prevent the formation of pyrogens, the intravenous and/or topical use of which is prohibited in areas in contact with the blood and lymph nodes. An innovative collection system has therefore been devised to obtain a sterile, allergen-free compound, without preservatives or pyrogens.

Figure 2:
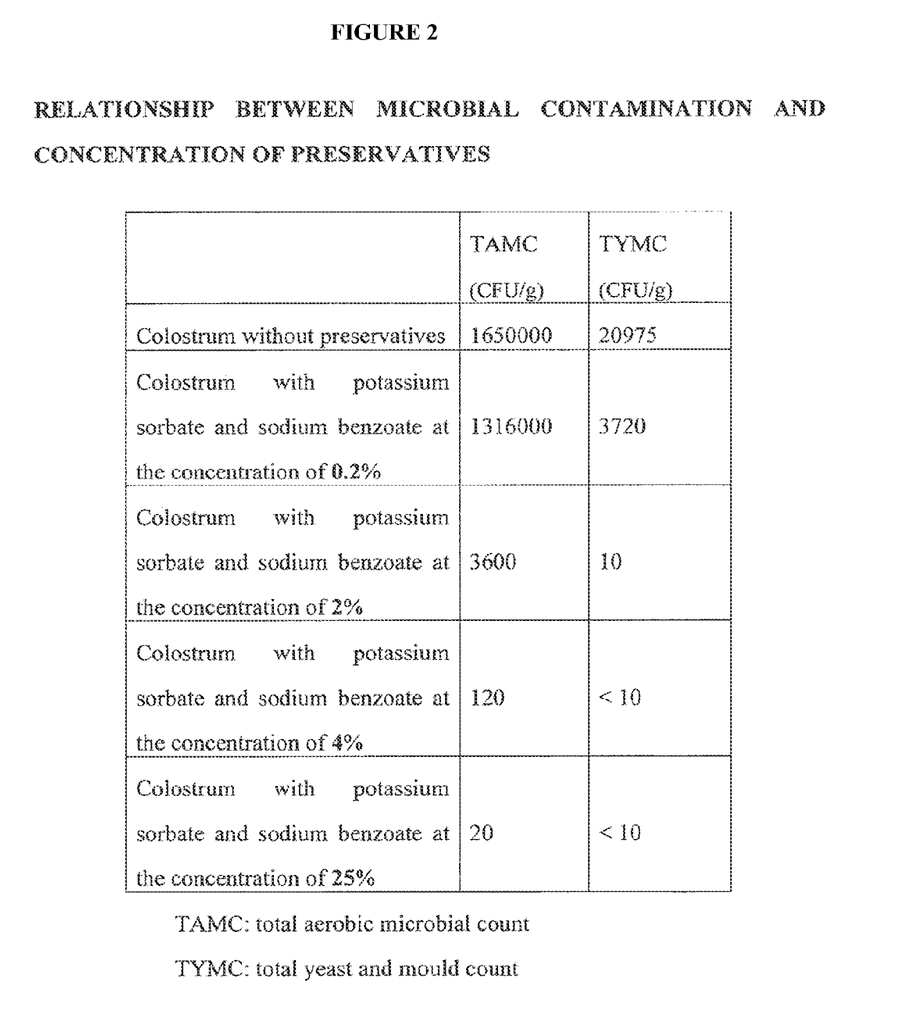
FIG. 2 shows the relationship between microbial contamination and concentration of preservatives in the colostrum collected in sterile tanks
Figure 3:
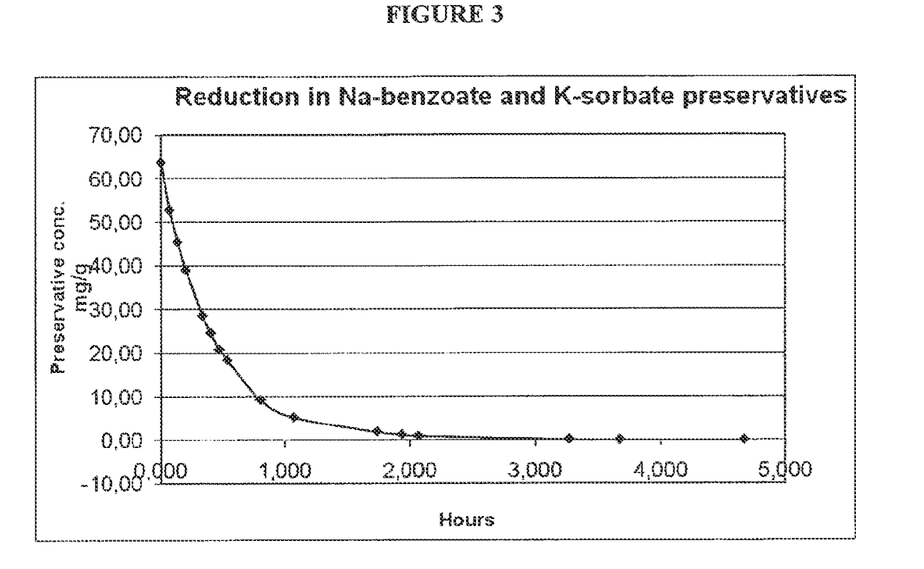
FIG. 3 shows the reduction in Na-benzoate and K-sorbate preservatives in the colostrum collected in sterile tanks

Antiseptic agents in sufficient quantities to guarantee sterility and absence of pyrogens are added to the colostrum collected in sterile tanks (which are sterilised empty at 25 Kgy) (FIG. 2). Potassium sorbate and sodium benzoate are preferably used, each at the concentration of 12.5% (a much higher concentration than normally used, namely 0.2%), or alternatively, phenoxyethanol at the concentration of 2.5% or diazolidinyl urea at the concentration of 1% (FIG. 3).

The colostrum thus treated does not need to be stored frozen before the active factor extraction processes, which leads to an obvious saving of industrial costs.

The colostrum is then diluted with saline solution: this dilution not only gives better filtration without clogging the filter pores, but above all allows the release of active factors bonded to fats and casein. The colostrum thus diluted undergoes tangential microfiltration (ceramic membranes with a cut-off between 2 and 6 μm, temperature 5/20° C., transmembrane pressure between 0.2 and 2 bars), which may be repeated, to obtain an opalescent solution free of casein, fat matrix and milk proteins. All these substances constitute over 90% of the allergic content of colostrum and cow's milk. The solution is then passed through membranes, or alternatively a molecular sieve with a cut-off at 300,000 daltons, for further purification of the active factors, all weighing less than 200,000 daltons.

Figure 4:
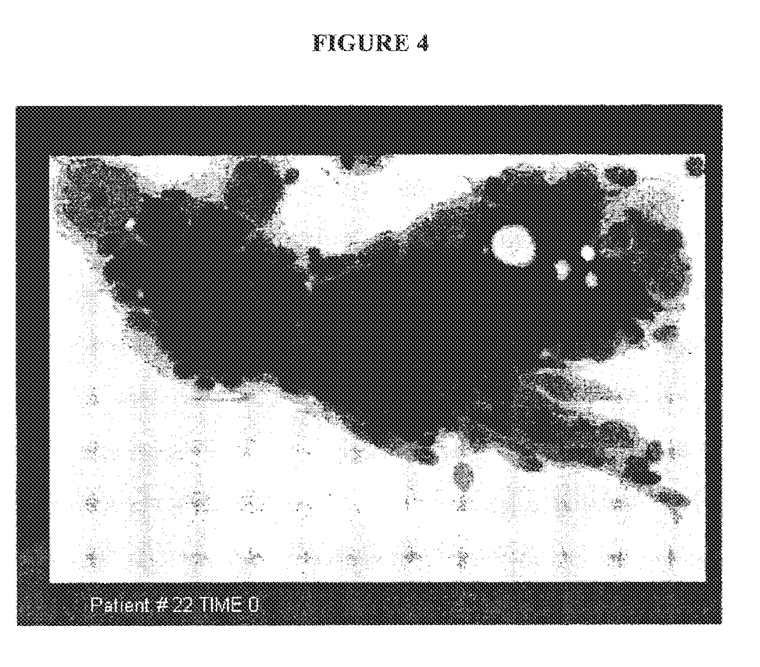
FIGS. 4-7 are cytological test performed after treatment with the vaginal gel.
Figure 5:
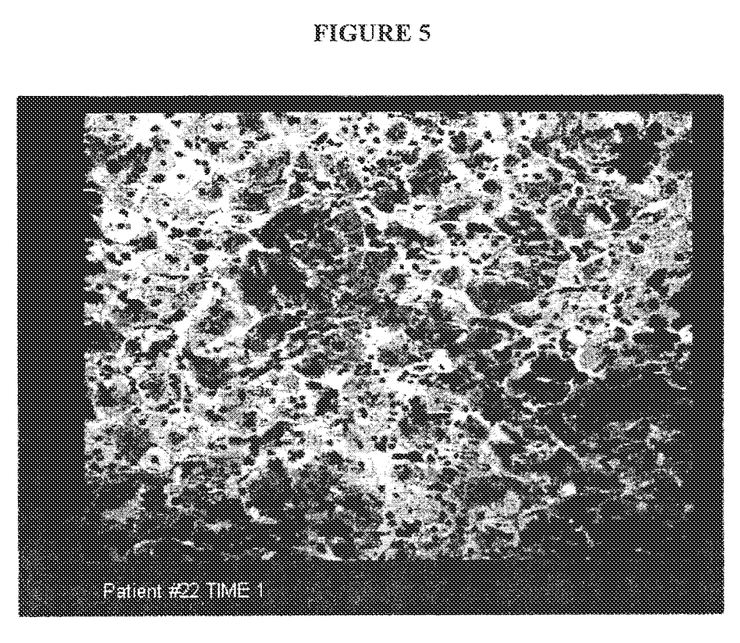
Figure 6:
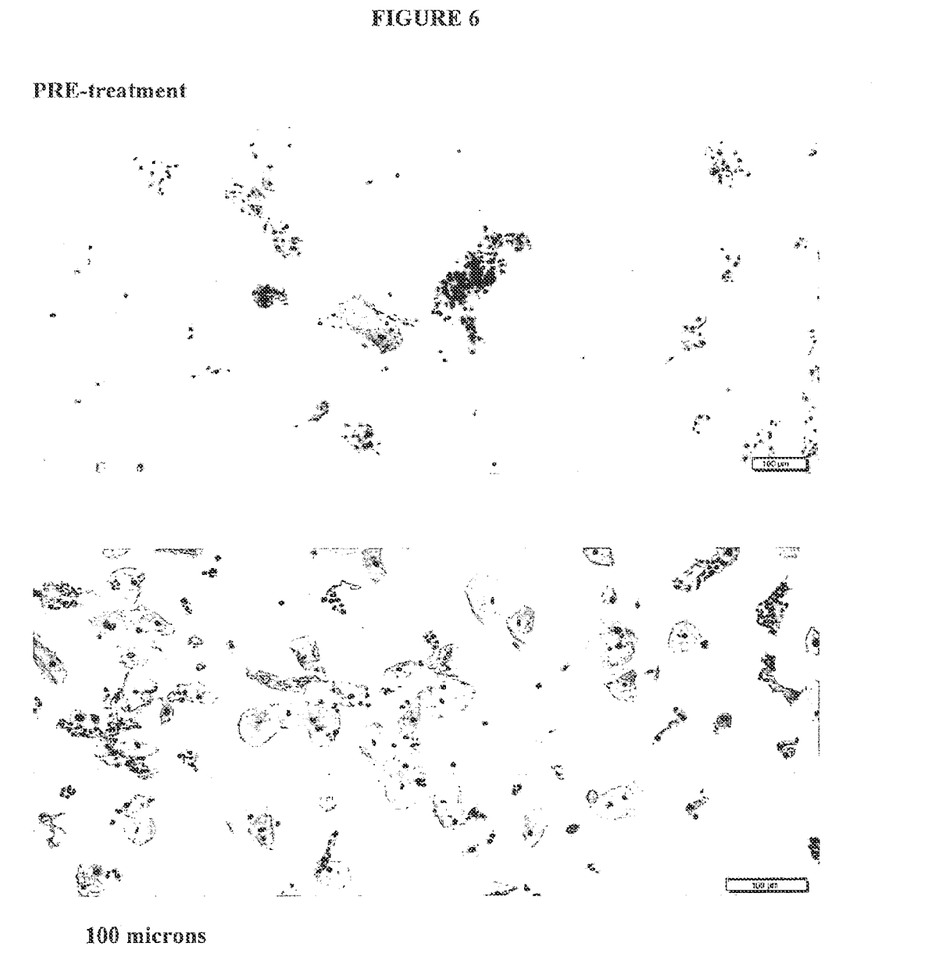
Figure 7:
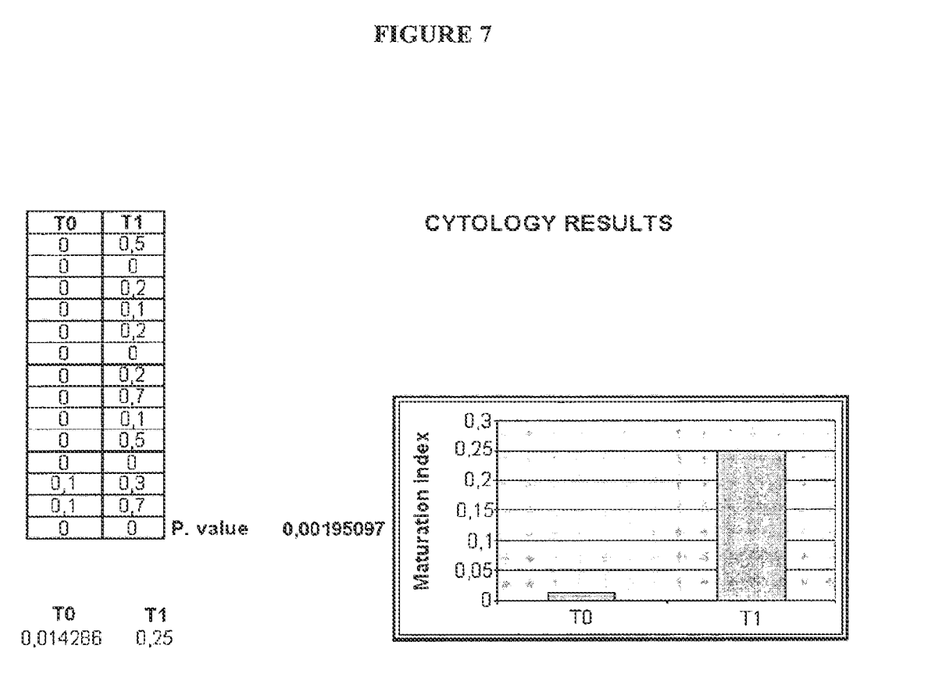

The solution is then dialysed by ultrafiltration (cut-off 1000/2000 daltons) at high pressure to totally eliminate the preservatives (molecular weight under 150 daltons), and then immediately freeze-dried (FIG. 4). The result is a sterile, pyrogen-free, preservative-free, anallergic powder (casein and lactoalbumin are responsible for over 95% of allergies to cow's milk) of very high solubility, with the maximum possible concentration of active factors.

This fraction, hereinafter called LIFEINSIDE™ Mucosa, contains the following factors:

Immune Mediators

Immunoglobulins of class IgG2 and IgA (ã/mg), in the proportion of approx. 60% of the Lifeinside™ Mucosa content (approx. 50% IgG2 and approx. 10% IgA), with natural specificity against many bacteria and viruses, some of which are responsible for superimposed NEC infection.

COMPLEMENT C3/C4: The complement consists of circulating proteins able to interact with the biological membranes and with specific receptors situated on the surface of various cell types, which induce inflammatory reactions that help combat infection.

Antibacterial/Antiviral Factors
Transferrin;
Lactoferrin;
Lysozyme;
Lactoperoxidase.

Growth Factors

TGF-β1—TRANSFORMING GROWTH FACTOR: stimulates the production of Class A immunoglobulins, which are responsible for immune defences in the mucosa. Modulates cell proliferation and stimulates the deposit of extracellular matrix.

EGF—EPIDERMAL GROWTH FACTOR: regulates the development of the mucosa. Promotes the formation of epithelial cells.

IGF 1—INSULIN-LIKE GROWTH FACTOR: modulates cell proliferation, adhesion and migration and induces maturity of the mucosa.

VEGF—VASCULAR ENDOTHELIAL GROWTH FACTOR: stimulates blood vessel production. Presents mitogenic activity and activation of vascular permeability.

FGF-b—FIBROBLAST GROWTH FACTOR BASIC: stimulates proliferation of cells of mesenchymal origin such as fibroblasts, endothelial cells, astrocytes and keratinocytes. Acts as a chemotactic and phytogenetic factor.

GH—GROWTH HORMONE: general growth factor of all tissues.

GHRF—GROWTH HORMONE RELEASING FACTOR.

NGF—NERVE GROWTH FACTOR: stimulates activity and regulates growth and differentiation of the sympathetic system.

PRP—Proline Rich Protein: Stimulates maturity of the T cells and has a regenerating effect on the nervous system, the bone system and the mucosa.

Chemotactic Factors

EOTAXIN: binds to the chemokine receptors to recruit eosinophils to inflamed tissues.

IP-10-Chemochin ligand 10: induced by interferon gamma, and aggregates inflammatory cells.

MCP-1 Monocyte chemotactic factor-1: promotes aggregation of monocytes to inflamed tissues.

Cytokines

IL-2: induces proliferation of T lymphocytes.
IL-4: possesses anti-inflammatory activity.
IL-6: stimulates innate and adaptive immunity.
IL-9: regulator of haemopoietic cells, stimulates cell proliferation and prevents apoptosis.
IL-17: regulates the activities of NF-KB and boosts nitric oxide (NO) production.
IL-10: presents pleiotropic effects in immunoregulation and inflammation. Improves B cell survival, and therefore antibody production. Studies conducted on Knockout mice demonstrate that this protein is essential in immunoregulation of the mucosa. Interferon-gamma: presents known antiviral, antitumoral and immunoregulatory activities. Is a powerful macrophage activator, and activates cell-mediated activity against bacteria and viruses.

TNF-α—Tumour necrosis factor: stimulates the migration of neutrophils and monocytes to the site of infection.

The fraction containing the substances listed above can be advantageously associated with other compounds with complementary or otherwise useful activity. The following substances are preferred:

Betaine: Betaine (trimethylglycine) is a substance of plant origin extracted from sugarbeet. It is involved in transmethylation, the biochemical process essential for cell metabolism via which methyl groups (CH3) are transferred from one molecule to another. In the body, betaine loses a methyl group and is converted to dimethylglycine (vitamin B15); during this process, energy is produced, which is believed to be responsible for the beneficial effects of this compound: disappearance of inexplicable tiredness and favourable effect on the circulatory system, heart, allergies and cell respiration. Betaine is an ideal ingredient for products designed for the skin and mucosa, which are particularly sensitive and delicate, in view of its moisturising and wetting properties, which are useful to promote immediate moisturising of the vaginal mucosa.

Panthenol: Pantothenic acid and the corresponding reduced form, panthenol, is one of the vitamins most widely used in topical applications. It has proved effective as a softener, moisturiser and conditioner. It performs a number of essential functions:

- after penetration into the mucosa it acts as an internally active moisturiser because it has an excellent ability to retain moisture, thus making the skin soft and elastic;
- it stimulates cell proliferation and aids tissue repair;
- it promotes normal keratinisation;
- it promotes the healing of minor wounds, slight abrasions and small burns due to its soothing properties.

Vitamin E or tocopherol, a fat-soluble vitamin with marked antioxidant activity able to prevent the breakdown of vitamin A and fatty acids, with consequent formation of toxic catabolites and formation of free radicals and peroxides. Vitamin E enters the cellular respiration processes, fortifies the walls of the blood vessels, and has important favourable effects on the reproductive apparatus.

Sericin (MW 400,000): moisturising, film-forming, with acidity buffering ability. Reduces the aggressiveness of surfactants. Has a considerable affinity for hydrophobic proteins and excellent ability to retain water, both of which characteristics increase with molecular weight. Unlike hyaluronic acid, which is often used in vaginal moisturising products, the film-forming effect is not occlusive. In the case of intact sericin, the pleasant, therapeutic film-forming effect does not prevent the other factors from being absorbed by the vaginal mucosa.

Maca (*Lepidium meyenii* extract): is a little-known plant remedy and high-energy food. Its popularity is increasing due to its energy-giving, fertility-promoting and aphrodisiac effects. Maca extract contains glucosinolates and isothiocyanates with chemopreventive activity. In women, Maca extract promotes fertility, stimulates the libido, alleviates the symptoms associated with the menopause, attenuates menstrual pain and has an energising effect.

The constituents of Maca have no oestrogenic activity, as demonstrated in oestrogen-dependent breast cancer (MCF-7 tumour cells).

Aloe vera has useful regenerating, proteolytic, wound-healing, anti-inflammatory, antipyretic, analgesic, wetting, bacteriostatic, virustatic, fungicidal and anti-itching properties.

The gel formulations according to the invention are prepared according to known techniques, using conventional excipients. The concentration of colostrum fraction in free form can vary between 1 and 10%, while that in encapsulated controlled-release form varies between 0.1 and 5%.

The approximate concentration intervals for the other constituents, when present, are set out below:

Sericin: 0.5-5%

Panthenol: 0.1-1%

Betaine: 1-10%

Aloe vera extract: 1-5%

Vitamin E: 0.1-2%

*Lepidium meyenii* extract: 1-5%

The invention is described in greater detail in the following experimental part, given by way of example.

EXAMPLE 1

Qualitative and Quantitative Composition of a Vaginal Gel with Rapid and Slow Release of Active Factors

| FORMULA | % |
| --- | --- |
| LIFEINSIDE MUCOSA | 5.00 |
| BETAINE | 5.000 |
| PANTHENOL | 0.200 |
| SODIUM BENZOATE | 0.500 |
| POTASSIUM SORBATE | 0.500 |
| DIAZOLIDINYL UREA | 0.500 |
| INTACT SERICIN (400 Kd) | 3.000 |
| XANTHAN GUM | 0.200 |
| CARBOXYMETHYLCELLULOSE | 0.600 |
| AMMONIUM ACRYLOYLMETHYLTAURATE/VP COPOLYMER | 1.000 |
| VEGETABLE GLYCERIN FU | 5.000 |
| DIMETHICONE | 0.100 |
| *LEPIDIUM MEYENII* ROOT EXTRACT 0.5% (DRIED MACA EXTRACT 0.5%) | 2.00 |
| *ALOE BARBADENSIS* (*VERA*) GEL 10:1 | 0.500 |
| PEG-40 HYDROGENATED CASTOR OIL | 2.000 |
| PHENOXYETHANOL | 1.000 |
| TOCOPHEROL ACETATE (VITAMIN E) | 0.500 |
| PARFUM (NOLA PORTOFINO PARFUME) | 0.100 |
| HYDROXYETHYL ACRYLATE/SODIUM ACRYLOYLDIMETHIL TAURATE COPOLYMER, ISOHEXADECANE, POLISORBATE 60 (SIMULGEL INS 100) | 2.000 |
| LIFEINSIDE MUCOSA IN MUCOADHESIVE MICROSPHERES | 2.00 |
| 90% LACTIC ACID | 0.250 |
| EXCIPIENTS q.s. for | 100 |

EXAMPLE 2

Clinical Trials

The vaginal gel described in Example 1 was used on 30 fertile, premenopausal and menopausal women suffering from vaginal dryness due to hormonal or mechanical reasons, stress, unbalanced local treatments, breast-feeding, contraceptives, etc.

Table 1 shows the results of colposcopy with the Schiller Test on a group of 30 treated patients and 28 controls. The difference between the two groups at the end of the study was statistically significant ($p<0.05$).

TABLE 1

DISTRIBUTION OF SUBJECTS STUDIED ACCORDING TO
COLPOSCOPY RESULTS AND TREATMENT ARM

| OBSERVATION | | | Lifeinside mucosa | |
|---|---|---|---|---|
| | Start of Trial | End of Trial | Start of Trial | End of Trial |
| Schiller Test | | | | |
| Normal uptake | - | 5(17.9%) | - | 26(86.7%) |
| Uneven uptake | 28 (100%) | 23(82.1%) | 30(100%) | 4(13.3%) |

Table 2 shows the results for the presence and severity of vaginal dryness in the same groups. Once again, the difference was statistically significant (p<0.05, treatment with a single daily administration for 20 days).

TABLE 2

DISTRIBUTION OF SUBJECTS STUDIED ACCORDING
TO PRESENCE AND SEVERITY OF VAGINAL
DRYNESS AND TREATMENT ARM

| Vaginal dryness | Observation Start of trial | End of Trial | Lifeinside mucosa Start of trial | End of Trial |
|---|---|---|---|---|
| None | — | 12(42.9%) | — | 23(76.7%) |
| Mild | 22(78.6%) | 16(57.1%) | 13(43.3%) | 5(16.7%) |
| Moderate/ Severe | 6(21.4%) | — | 17(56.6%) | 2(6.7%) |

Use of the combined prompt- and delayed-release vaginal gel led to a definite improvement in the clinical picture and the symptoms associated with vaginal dryness. In the control group, only 16.7% of cases had improved after 20 days, whereas 86.7% of cases in the treatment group had improved/were cured.

The cytological test after treatment (FIGS. 4-7) demonstrates:
increased cellularity
a relative increase in mature squamous cells
a relative reduction in basal and para-basal cells.
presence of inflammation and multinuclear histiocytes indicating increased tropism.

The invention claimed is:

1. Topical vaginal compositions in gel form comprising a colostrum fraction, wherein said colostrum fraction is enriched with immunoglobulins, growth factors, chemotactic factors and antimicrobial/antiviral factors, and wherein said colostrum fraction is partly non-encapsulated and partly encapsulated in mucoadhesive microbeads.

2. Compositions as claimed in claim 1 comprising immunoglobulins of class IgG2 and IgA, complement c3/c4, transferrin, lactoferrin, lysozyme, lactoperoxidase, TGF-β1—transforming growth factor, EGF—epidermal growth factor, IGF 1—insulin-like growth factor, VEGF—vascular endothelial growth factor, FGF-b—fibroblast growth factor basic, GH—growth hormone, GHRF—growth hormone releasing factor, NGF—nerve growth factor, proline-rich proteins, eotaxin, IP-10-chemokine ligand 10, MCP-1 monocyte chemotactic factor-1, IL-2, IL-4, IL-6, IL-9, IL-17, IL-10, interferon-gamma, and TNF-α—tumour necrosis factor.

3. Compositions as claimed in claim 1, wherein the colostrum fraction is obtainable from bovine colostrum milked between the 5th and 6th hours after calving and wherein said colostrum fraction is treated with a process which comprises:
   adding antiseptic agents to the colostrum in sufficient concentrations to ensure sterility and apyrogenicity;
   diluting the colostrum with saline solution;
   performing one or more tangential microfiltration steps of the colostrum through ceramic membranes with cut-off ranging between 2 and 6 μm to obtain a solution;
   passing the solution through membranes or molecular sieves with cut-off of 300,000 Daltons;
   dialysing the solution by high-pressure ultrafiltration until complete removal of the antiseptic agents and final freeze-drying.

4. Compositions as claimed in claim 3 wherein the colostrum is obtained from Guernsey or Holstein cows.

5. Compositions as claimed in claim 1 further comprising one or more of the following ingredients:
   a) Sericin;
   b) Panthenol;
   c) Betaine;
   d) *Aloe vera* extract;
   e) Vitamin E; and
   f) *Lepidium meyenii* extract.

* * * * *